United States Patent
Akimoto

(10) Patent No.: US 7,718,912 B2
(45) Date of Patent: May 18, 2010

(54) OUTER SURFACE-INSPECTING METHOD AND OUTER SURFACE-INSPECTING APPARATUS

(75) Inventor: Shigeyuki Akimoto, Kawagoe (JP)

(73) Assignee: Kabushiki Kaisha TOPCON, Itabashi-Ku, Tokyo (JP)

( * ) Notice: Subject to any disclaimer, the term of this patent is extended or adjusted under 35 U.S.C. 154(b) by 289 days.

(21) Appl. No.: 11/302,148

(22) Filed: Dec. 14, 2005

(65) Prior Publication Data

US 2006/0182333 A1    Aug. 17, 2006

(30) Foreign Application Priority Data

Dec. 20, 2004    (JP)    ............... 2004-366935

(51) Int. Cl.
*B07C 5/00*    (2006.01)
(52) U.S. Cl. .................. 209/576; 209/539; 209/577; 382/144; 382/145; 382/147; 382/149
(58) Field of Classification Search ............. 209/539, 209/576, 577, 578, 579, 580, 581, 582; 382/144, 382/145, 147, 149, 209, 218
See application file for complete search history.

(56) References Cited

U.S. PATENT DOCUMENTS

| | | | |
|---|---|---|---|
| 5,808,735 A | | 9/1998 | Lee et al. |
| 6,810,139 B2 * | | 10/2004 | Smilansky et al. .......... 382/149 |
| 7,257,247 B2 * | | 8/2007 | Bruce et al. ................ 382/144 |
| 7,275,005 B2 | | 9/2007 | Baba et al. |
| 2003/0034282 A1 * | | 2/2003 | Safai .......................... 209/582 |
| 2006/0182334 A1 | | 8/2006 | Akimoto |
| 2007/0058853 A1 * | | 3/2007 | Minakata et al. ........... 382/145 |
| 2007/0117029 A1 * | | 5/2007 | Ibusuki ........................ 430/5 |
| 2007/0230769 A1 * | | 10/2007 | Yasumoto et al. ........... 382/149 |

FOREIGN PATENT DOCUMENTS

| | | | |
|---|---|---|---|
| JP | 2004-085543 A | | 3/2004 |
| JP | 2004085543 A | * | 3/2004 |
| JP | 2004-132950 A | | 4/2004 |
| JP | 2004132950 A | * | 4/2004 |

OTHER PUBLICATIONS

U.S. Office Action in corresponding U.S. Appl. No. 11/302,149 dated Dec. 31, 2008.
Office Action issued Jul. 16, 2009 in U.S. Appl. No. 11/302,149, available on line at USPTO web site.

* cited by examiner

*Primary Examiner*—Patrick Mackey
*Assistant Examiner*—Kalyanavenkateshware Kumar
(74) *Attorney, Agent, or Firm*—Buchanan Ingersoll & Rooney PC

(57) ABSTRACT

A outer surface-inspecting method for judging whether a defect of a defective portion (27) extracted from an inspection area in an image (21A) of an object to be inspected through comparison with a template is acceptable or not, including: dividing the inspection area into a plurality of sections (22, 23, 24a, 24b, 25a, 25b, 28a, 28b, 28c) respectively having different acceptable levels (CONDITION 1-6); judging, when at least one extracted defective portion (27) spreads out over some of the sections (28a, 28b, 28c) respectively having different acceptable levels, whether the defect of the defective portion (27) is acceptable or not based on a strictest acceptable level (CONDITION 3) of all the acceptable levels (CONDITION 3-5) respectively set on the plurality of sections (28a, 28b, 28c) on which the defective portion (27) is located.

4 Claims, 7 Drawing Sheets

CONDITION 1
CONDITION 2
CONDITION 3
CONDITION 4
CONDITION 5
CONDITION 6

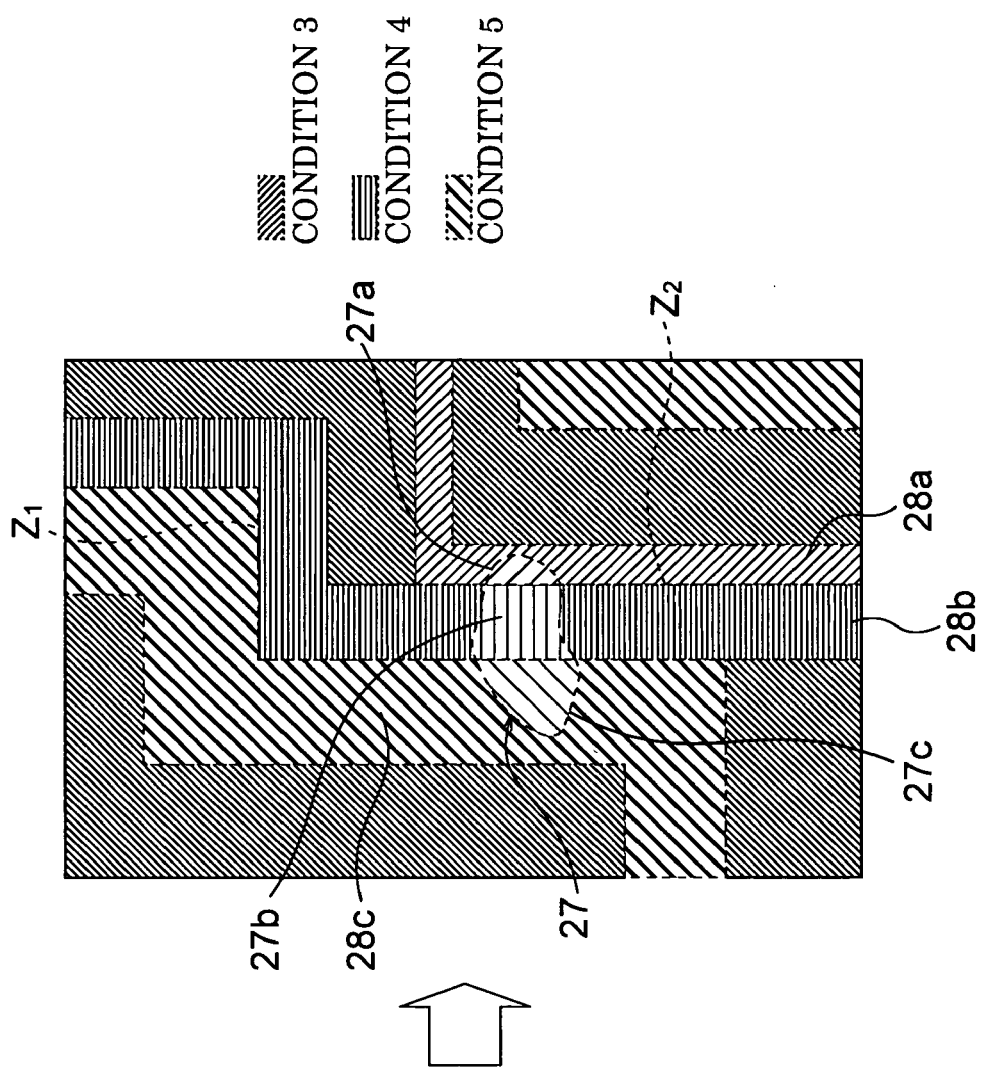

OUTER SURFACE-INSPECTING METHOD AND OUTER SURFACE-INSPECTING APPARATUS

BACKGROUND

1. Field of the Invention

The present invention relates to a method for inspecting an outer surface of an object to be inspected and an apparatus therefor. Particularly, the present invention relates to an outer surface-inspecting method and an outer surface-inspecting apparatus suitable for judging whether a defect of a circuit pattern formed on a semiconductor chip is acceptable or not, the defect being caused by a gap of the circuit pattern, a foreign body attached to the circuit pattern, or the like.

2. Description of Related Art

There is used a method using a template as an outer surface-inspecting method for judging whether a circuit pattern is good or not. There is proposed a method including: photographing an outer surface image of one good pattern selected as a template; detecting a pattern shape by carrying out an edge detection process on the photographed image; and automatically dividing an area to be inspected based on the pattern shape into a plurality of sections (e.g., Japan Patent Application Laid-Open No. 2004-85543 (paragraphs 0029-0057 and FIG. 3)). Also, in order to set each section on an area to be inspected according to a detected pattern, there is used a method including: setting layers respectively for inspection conditions based on acceptable levels as to defects; and setting sections respectively having acceptable levels different from each other, which are classified and divided by superposing the layers (e.g., Japan Patent Application Laid-Open No. 2004-132950 (paragraphs 0032-0065 and FIG. 3)).

In such prior art described above, the template and an image obtained from an object to be inspected are compared over each inspection area. When a defect of the object to be inspected is extracted by the comparison, it is judged whether or not the level of the extracted defect exceeds a predetermined acceptable level of a corresponding section. For example, when a spread of the extracted defect is compared to a predetermined acceptable value of a corresponding section where the defect exists and the spread exceeds the acceptable value, the object to be inspected is judged as a defective product.

According to the prior art, set sections can be set automatically by image-processing a photographed image obtained from the object to be inspected. Further, by superposing a plurality of the layers respectively having acceptable levels different from each other, the area to be inspected can be divided into set sections respectively having different acceptable levels, corresponding to a desirable condition. Thus, an operator can easily operate an inspecting apparatus, and a workload of the operator may be reduced.

However, according to the prior art, a centroid method is used for judging whether a defective portion extracted through comparison with the template exceeds a corresponding acceptable level or not. According to the centroid method, as an acceptable level for judging one defective portion consisting of a collective entity of defects, an acceptable level only corresponding to one set section where the centroid of the defective portion is located is chosen.

Thus, when a defective portion spreading out over a plurality of sections respectively having different acceptable levels is found, acceptable levels of sections out of which the centroid is located are not taken into consideration, although one/some parts of the defective portion are located on such sections. That is, when a defective portion spreading out over a plurality of set sections respectively having different acceptable levels exists and the centroid of the defective portion is located on one of the set sections having the lowest acceptable level of all the acceptable levels of the set sections, the lowest acceptable level, i.e., the most strict acceptable level is compared to the defect of the entire defective portion. Similarly, when the centroid of the defective portion is located on another set section having the highest acceptable level, i.e., the lightest acceptable level of all the acceptable levels of the set sections, the lightest acceptable level is compared to the defect of the entire defective portion. Thus, even if there are defective portions respectively having the same area thereof, acceptable levels applied for judgments of the defects of those defective portions may be widely changed according to a slight difference of centroid positions due to a slight difference in shapes/positions between the defective positions and therefore their judgments may result in the opposite.

Even if a defect of a defective portion does not exceed an acceptable level of a set section on which the centroid of the defective portion is located and in the case a part of the defective portion spreads out over a section(s) having an acceptable level more strict than that of the set section where the centroid is positioned, a defect of the part of the defective portion located on the section may exceed the acceptable level of the section on which the centroid is not located. In such case, the acceptable level of the section on which the centroid is not located is not taken into consideration according to the conventional centroid method, thus, it may be overlooked that the defect of the part of the defective portion spreading out over the section on which the centroid of the defective portion is not located exceeds the strict acceptable level of the section out of the centroid. As a result, it may be erroneously judged as a good product.

SUMMARY

The present invention has been made in consideration of above mentioned actualities. The present invention provides an outer surface-inspecting method and an apparatus therefor capable of more precisely judging whether a defect of a to-be-inspected object is acceptable or not.

One feature of an outer surface-inspecting method configured to judge whether a defect of a defective portion extracted from an inspection area in an image of an object to be inspected through comparison with a template is acceptable or not according to the present invention is that the method includes: dividing the inspection area into a plurality of sections respectively having different acceptable levels; judging, when at least one extracted defective portion spreads out over some of the sections respectively having different acceptable levels, whether the defect of the defective portion is acceptable or not based on a strictest acceptable level of all the acceptable levels respectively set on the plurality of sections on which the defective portion is located.

According to the outer surface-inspecting method of the present invention, when a defective portion is located on a plurality of sections, a judgment whether the defect of the defective portion is acceptable or not is made based on the strictest acceptable level of all acceptable levels respectively set on the plurality of sections on which the defective portion is located, regardless of the position of the centroid of the defective portion. Thus, even if a part of the defective portion located on the section having the strictest acceptable level does not have the centroid of the defective portion therein, the strictest acceptable level is used in judgment.

Thus, an overlooked error as to such defect of the part of the defective portion whose centroid is out of the part can be eliminated.

Thus, the method of the present invention can judge whether a defect of a defective portion is acceptable or not more precisely and unfailingly than a conventional method can.

Preferably, the outer surface-inspecting method according to the present invention further includes: judging whether the defect of the defective portion spreading out over the plurality of the sections is acceptable or not with use of the acceptable level of the section on which a centroid of the defective portion is located, wherein whether the defect of the defective portion is acceptable or not is judged through comparison of the result of the judgment made based on the strictest acceptable level and the result of the judgment made with use of the acceptable level of the section on which the centroid is located.

The preferred outer surface-inspecting inspection method according to the present invention can estimate a judgment result obtained through a conventional centroid method in addition to the judgment result obtained with use of the strictest acceptable level of all acceptable levels respectively set on the plurality of the sections on which the defective portion is located. Thus, the judgment result based on the judgment obtained by using the strictest acceptable level of all acceptable levels respectively set on the plurality of the sections on which the defective portion is located and the judgment result obtained through the conventional centroid method can be used according to need and then a final judgment whether the defect of the defective portion is acceptable or not can be made. Thus, more proper judgment according to a situation is enabled.

Preferably, according to the outer surface-inspecting method of the present invention, the sections are set based on superposition of layers respectively formed in conformity with different inspection conditions as to a defect.

According to the preferred outer surface-inspecting inspection method of the present invention, the inspection area can be divided into set sections respectively having different acceptable levels under a desired condition by superposing the plurality of layers having different acceptable levels. Thus, an operator can easily handle an inspection apparatus and therefore the workload of the operator can be reduced.

Preferably, according to the outer surface-inspecting method of the present invention, acceptable defect pixel numbers as threshold values representing acceptable levels are respectively set for the plurality of the sections, and whether the defect of the defective portion is acceptable or not is judged by comparing an acceptable defect pixel number corresponding to the strictest acceptable level with a pixel number corresponding to the defective portion.

According to the preferred outer surface-inspecting method of the present invention, the judgment whether the defect of the defective portion is acceptable or not can be carried out by comparing the number of pixels corresponding to the defective portion with the lowest acceptable defect number of pixels of all the acceptable pixel numbers respectively set on the sections.

One feature of an outer surface-inspecting apparatus according to the present invention, including: an image-pickup portion configured to obtain an image of an object to be inspected; an arithmetic calculation processing circuit configured to carry out an edge detection process on the image obtained by the image-pickup portion; and a monitor configured to display the image obtained by the image-pickup portion and the image processed by the arithmetic calculation processing circuit, wherein the arithmetic calculation processing circuit has: a section-setting portion configured to divide an inspection area of a pattern image obtained through the edge detection process into a plurality of sections to which different threshold values representing acceptable levels as to a defect are respectively allotted; a defect-extracting portion configured to extract a defective portion of the object to be inspected by comparing a template to the image of the object to be inspected; and a judging portion configured to compare the strictest threshold value of all the threshold values respectively set on the sections on which the defective portion extracted by the defect-extracting portion is located with the defects of the defective portion and configured to output a result of the comparison to the monitor.

According to the outer surface-inspecting apparatus of the present invention, the section-setting portion, the defect-extracting portion and the judging portion are provided in the arithmetic calculation processing circuit. The inspection area of the pattern image obtained through the edge detection process is divided by the section-setting portion into plural sections respectively representing different acceptable levels as to defects. The defective portion of the to-be-inspected object is extracted by the defect-extracting portion. The strictest threshold value of all the threshold values respectively set for the sections on which the defective portion extracted by the defect-extracting portion is located and the defects of the defective portion are compared by the judging portion. The result of the comparison is outputted to the monitor. Thus, the outer surface-inspecting apparatus can carry out the outer surface-inspecting method(s) of the present invention relatively easily.

According to the outer surface-inspecting method/apparatus of the present invention, the strictest acceptable level of all the acceptable levels respectively set on the sections on which the defective portion is located is used for judging whether the defect of the defective portion is acceptable or not. Thus, defect inspection for a to-be-inspected object such as a semiconductor chip on which a circuit pattern is formed can be carried out more faithfully through the inspection method of the present invention, eliminating an erroneous judgment where a non-defective product is judged as a defective product, than it can be done through a conventional inspection method.

These and other objects, features and advantages of the invention will be appreciated upon reading of the description of the invention when in conjunction with the attached drawings, with the understanding that some modifications, variations and changes of the invention could be easily made by the skilled person in the art to which the invention pertains without departing from the spirit of the invention or the scope of the claims.

The present application is based on, and claims priority from, Japanese Patent Application No. 2004-366935, filed on Dec. 20, 2004, the contents of which are hereby incorporated by reference herein in its entirety.

BRIEF DESCRIPTION OF THE DRAWINGS

For a better understanding of the invention, reference is made to the attached drawings, wherein:

FIG. 5A and FIG. 5B are explanatory views respectively showing examples of an extracted defective portion and acceptable defect levels set for each section on which the defective portion is located.

DETAILED DESCRIPTION OF THE PREFERRD EMBODIMENTS

Hereinafter features of the present invention will be described in detail, referring to an embodiment shown in the accompanied figures.

Figure 1:
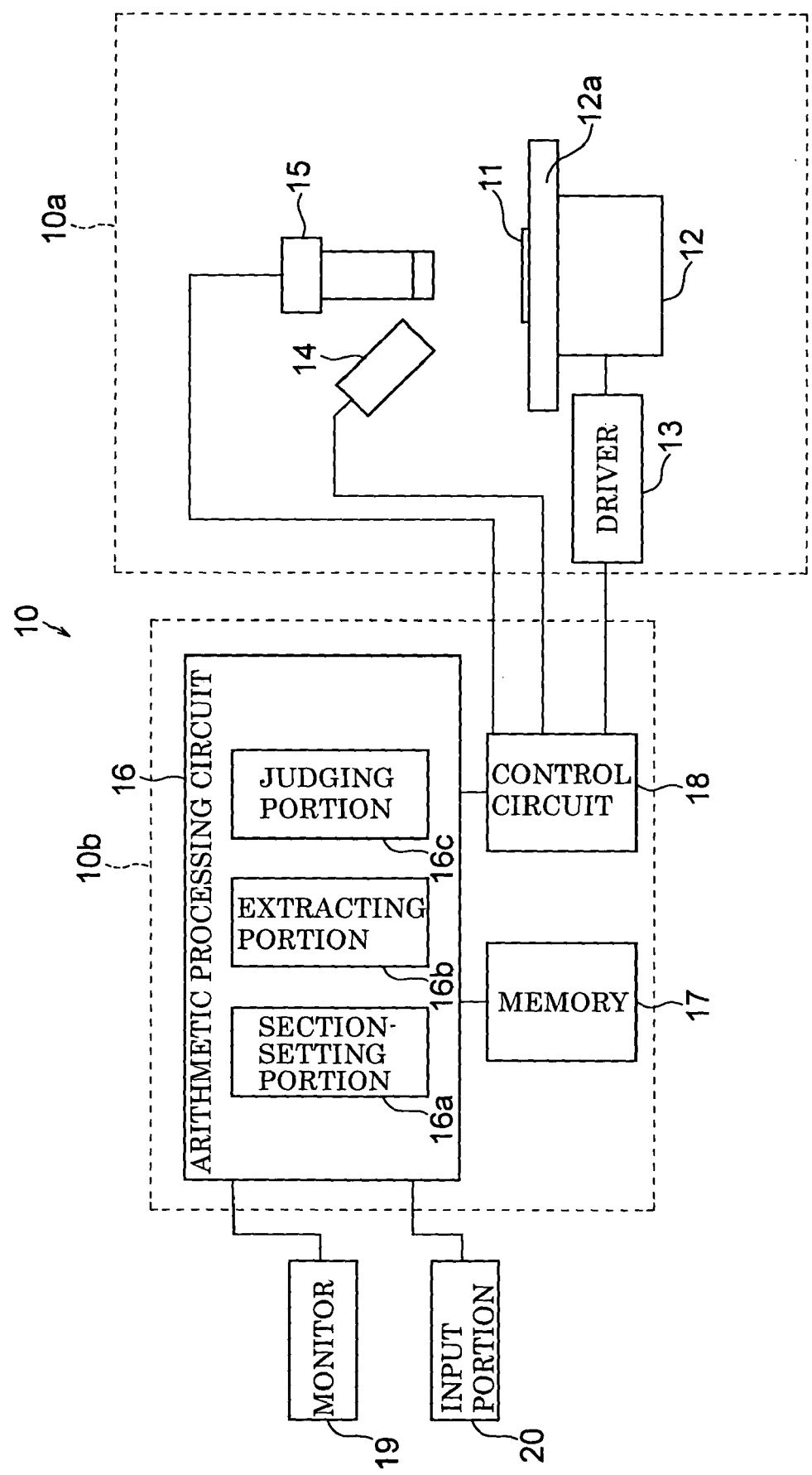
FIG. 1 is a block diagram schematically showing an outer surface-inspecting apparatus configured to execute an outer surface-inspecting method according to the present invention.
Figure 2:
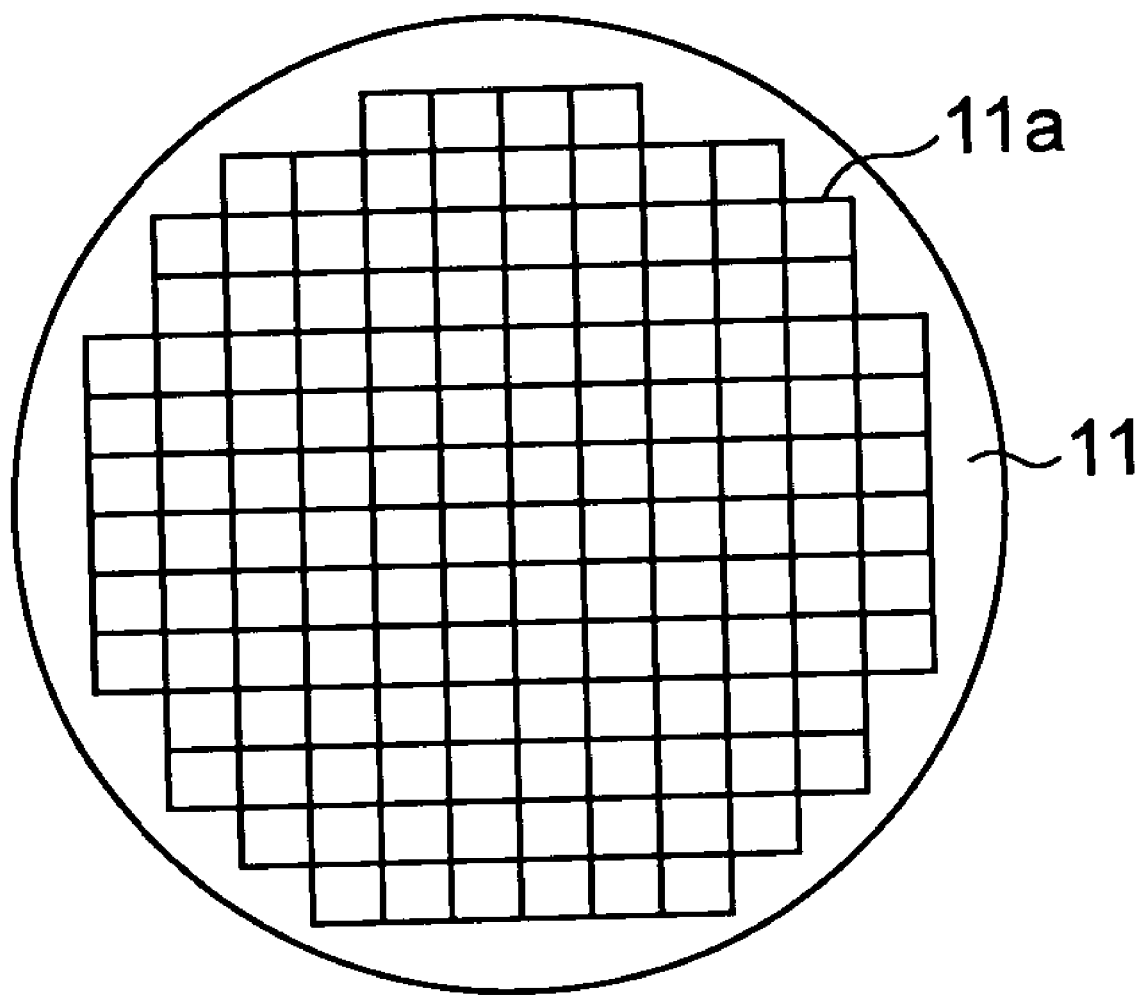
FIG. 2 is a plan view showing a semiconductor wafer as an example of a to-be-inspected object for the outer surface-inspecting method of the present invention.

FIG. 1 shows an outer surface-inspecting apparatus 10 suitable for performing an outer surface-inspecting method according to the present invention. The outer surface-inspecting apparatus 10 is used for judging whether a defect(s) of, for example, circuit patterns respectively formed on a plurality of semiconductor chips 11a orderly formed on a semiconductor wafer 11 as shown in FIG. 2 is acceptable or not. The present invention will be described below in accordance with an example where the present invention is applied to inspection of a semiconductor chip 11a formed on the semiconductor wafer 11.

The outer surface-inspecting apparatus 10 according to the present invention is, as shown in FIG. 1, provided with an optical image-pickup structure 10a and a control/arithmetic device 10b for controlling the operation of the optical image-pickup structure 10a and for arithmetically processing image information obtained by the optical image-pickup structure 10a.

The optical image-pickup structure 10a is provided with a movable portion 12 having a stage 12a for holding the semiconductor wafer 11, a driver 13 for rotating the stage 12a of the movable portion 12 around an X-axis, a Y-axis and a Z-axis on a XY plane, an image-pickup portion 15 for taking a surface image of a desired semiconductor chip 11a, being formed on the semiconductor wafer 11 disposed on the stage 12a under lighting of a lighting device 14. The image-pickup portion 15 includes, for example, a CCD and an optical system thereof, as well known in the conventional art.

The control/arithmetic device 10b includes an arithmetic processing circuit 16. The arithmetic processing circuit 16 may consist of, for example, a central processing unit (CPU) capable of operating in accordance with a program stored in a memory 17. The arithmetic processing circuit 16 controls the driver 13 of the optical image-pickup structure 10a, the lighting device 14 and the image-pickup portion 15 via a control circuit 18 and carries out an edge detection process on an image taken by the image-pickup portion 15 in accordance with information stored in the memory 17.

The arithmetic processing circuit 16 is provided with a section-setting portion 16a for dividing an inspection area of the image obtained by the image-pickup portion 15 into a plurality of sections, a defect extracting portion 16b for extracting a defective portion by way of comparing the inspection area of the image with a template for inspection, and a judging portion 16c for judging whether the defective portion extracted by the extracting portion 16b is acceptable or not.

A monitor 19 having a display portion consisting of LCD, CRT or the like and an input portion 20 including a keyboard and a mouse or the like are connected to the arithmetic processing circuit 16. An image taken by the image-pickup portion 15, an image processed by the arithmetic processing circuit 16, and information necessary for the operation of the optical image-pickup structure 10a can be displayed on the monitor 19. A command necessary for the operation of the outer surface-inspecting apparatus 10 can be properly inputted with the input portion 20 based on the information displayed on the monitor 19.

Figure 3A:
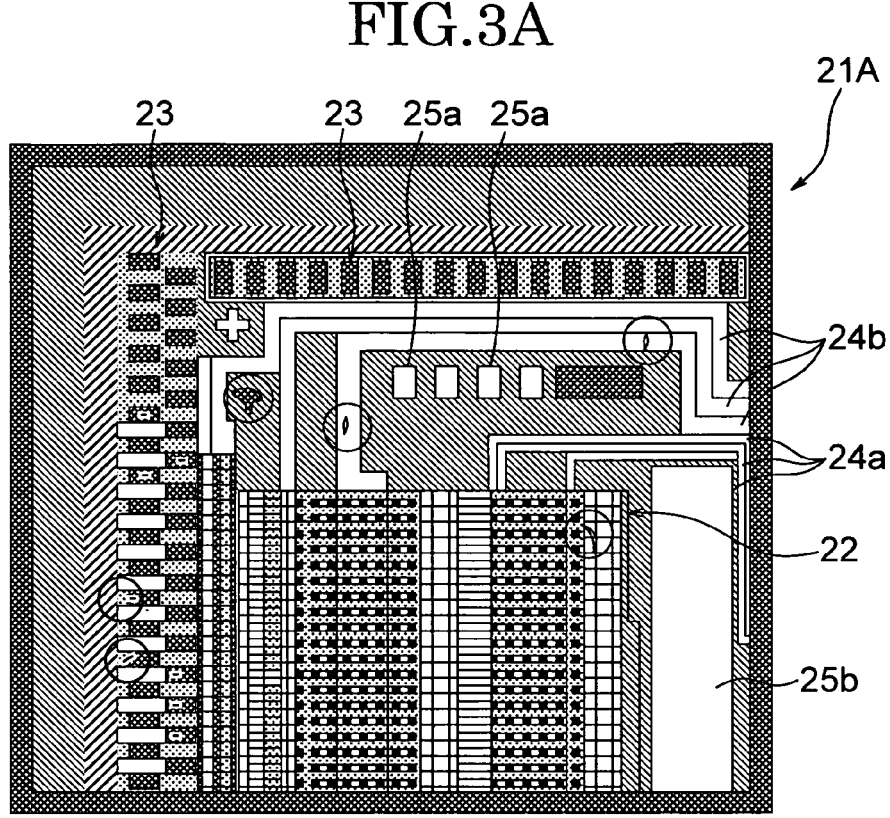
FIG. 3A is an explanatory view showing an example of an image obtained by an image-pickup device of the outer surface-inspecting apparatus shown in FIG. 1.

The image-pickup portion 15 takes images of the template and an object to be inspected ("a to-be-inspected object"). A desired inspection area is clipped from the surface image of the semiconductor chip 11a taken by the image-pickup portion 15, and is displayed on the monitor 19. An example of a display screen 21A of this clipped image is shown in FIG. 3A. The display screen 21A shows an example where the semiconductor chip 11a is a memory chip. In the display screen 21A, a memory device area 22, pad areas 23, electricity-conducting paths 24a and 24b, electricity-conducting portions 25a and 25b, etc. formed on the semiconductor chip 11a are shown. In the display screen 21A, defective portions respectively consisting of aggregations of defects are observed within circular marks. The observed defects may be a foreign body attached to the circuit pattern, a partial gap of the circuit pattern, or the like.

A display image (21A) of a semiconductor chip 11a having the highest quality with few defects consisting of a gap/foreign body can be chosen from the surface images 21A respectively obtained from semiconductor chips 11a of the semiconductor wafer 11 and be used as a template. This template and a display image 21A of another semiconductor chip 11a as an object to be inspected are compared by the arithmetic processing circuit 16 for extracting a defect of the object.

As it is conventionally well-known, the arithmetic processing circuit 16 performs preprocessing for a edge detection process on a surface image (21A) for the template taken by the image-pickup portion 15 as well as each surface image 21A of the objects to be inspected before a comparison process of the template and images of the semiconductor chips 11a as the objects to be inspected. As preprocessing for the edge detection process, there are conventionally well-known a shading process for diminishing unevenness of lighting of the lighting device 14, a value multiplexing process for further clarification of edges, a hue modification process for reducing effect of a hue of an image and/or a density of patterns in edge detection, an expansion-contraction process using a expansion-contraction filter for reducing noise or shifting chromaticity for simplifying cognizance of a pattern, and the like. Those processes can be appropriately selected for the present invention.

The arithmetic processing circuit 16 carries out an edge detection process on the preprocessed image. As edge detection process conventionally well-known, edge detection schemes using differentiation or the like may be applied. The arithmetic processing circuit 16 can detect the circuit pattern of the inspection area (21A) with this edge detection process.

The section-setting portion 16a of the arithmetic processing circuit 16 divides the circuit pattern extracted through the edge detection process into sections in accordance with an inspection condition imputed from the input portion 20. The section-setting portion 16a respectively allots the sections inspection conditions which represent acceptable ranges of defects. Thus, a section-setting process is executed on the surface image 21A of the inspection area shown in FIG. 3A. That is, as represented by a section-setting image 21B of FIG. 3B, sections (22, 23, 24a, 24b, 25a, 25b) to which inspection conditions 1-6 are respectively allotted are set on the inspection area.

The most strict inspection condition 1 of all conditions (1-6) is allotted to the section (22) corresponding to the memory device area 22 whose defect is considered to be most influential of all defects of sections (22, 23, 24a, 24b, 25a, 25b). Numerals 1-6 of inspection conditions represent the strictness of condition levels, and in this example, the number becomes bigger, the condition becomes lesser strict. For example, the inspection condition 6 represents the lightest condition level. Specifically, the inspection conditions 2-6 are respectively allotted in numeric order to the sections (23, 24a, 24b, 25a, 25b) respectively corresponding to the narrow electricity-conducting paths 24a, the electricity-conducting paths 24b whose width is wider than that of the electricity-conducting paths 24a, the small electricity-conducting portions 25a, the electricity-conducting portion 25b whose area is larger than that of the electricity-conducting portion 25a, and pad areas 23 whose defects are considered to have the smallest influence of those of all sections (22, 23, 24a, 24b, 25a, 25b).

For example, the method disclosed in Japan Patent Application Laid-Open No. 2004-85543, also mentioned in the Description of Related Art, may be used in order to divide the inspection area into sections. A circuit pattern on an inspection area can be automatically detected and the inspection area whose pattern is detected can be automatically divided into the sections. Further, for example, the "layer scheme" disclosed in Japan Patent Application Laid-Open No. 2004-13295, also mentioned in the Description of Related Art, enables simple section setting.

Figure 4B:
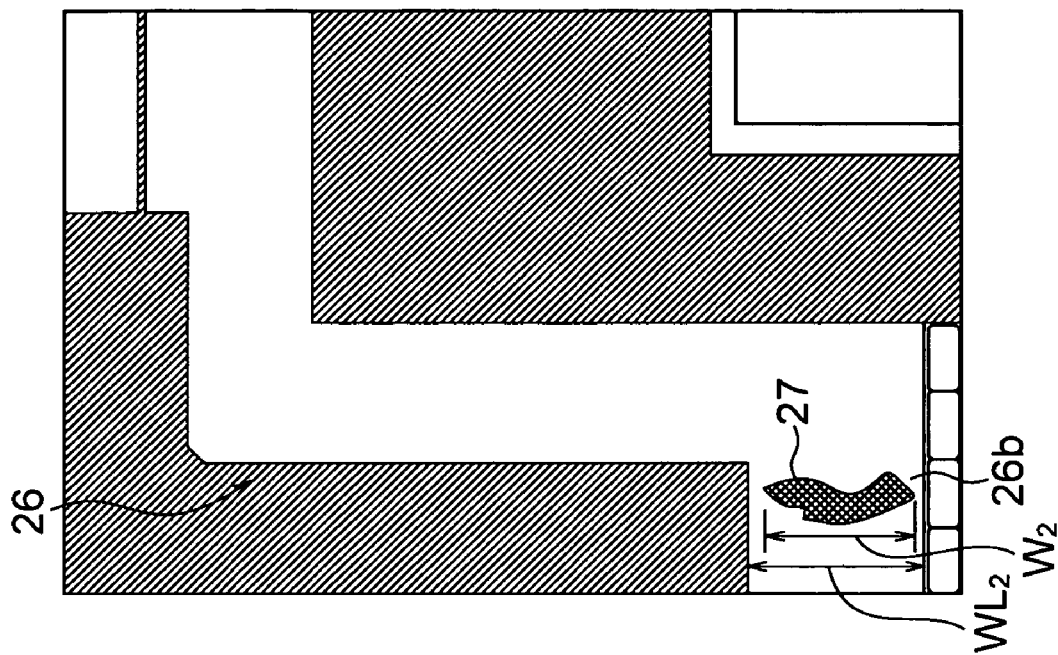
FIG. 4B is an explanatory view showing another setting example of an inspection condition for the section shown in FIG. 4A.

Acceptable ranges (i.e., acceptable levels) for a defect such as a gap/foreign body which is an inspection target are adopted as an inspection condition. As to acceptable range, different values can be respectively allocated to sections in light of a measure and/or a position and/or a function of each section. That is, as shown in FIGS. 4A and 4B, even if defective portions respectively having the same area and shape are located on a pattern, estimation of the defective portions varies depending on positions of the defective portions.

Figure 4A:
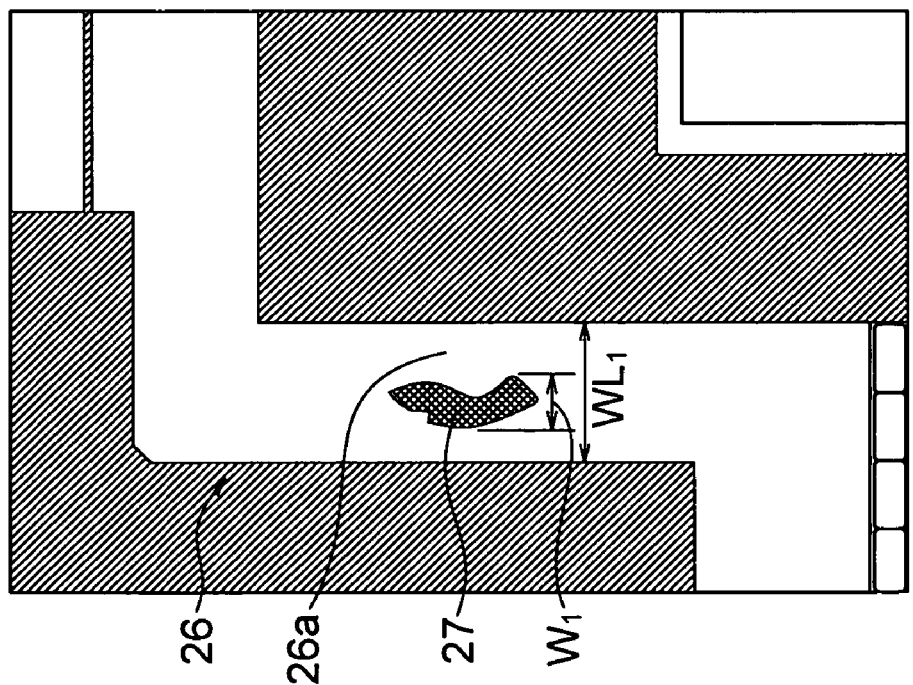
FIG. 4A is an explanatory view showing a setting example of an inspection condition for a section.

Referring to one example shown in FIG. 4A, on a longitudinal portion 26a of an electricity-conducting path 26 which extends in a longitudinal direction, a defective portion 27 extending in the extending direction of the longitudinal portion 26a is observed. On the other hand, the other example shown in FIG. 4B, the defective portion 27 is positioned on a lateral portion 26b of the electricity-conducting path 26 which extends in a lateral direction, such that the defective portion 27 crosses over the lateral portion 26b. Both of the defective portions 27 have the same shape and square measure and exist on the electricity-conducting path 26 with the same posture. However, according to the example shown in FIG. 4A, a width measure W1 of the defective portion 27 along a width measure WL1 of the longitudinal portion 26a have a great influence on the electricity-conductive function of the electricity-conducting path 26, whereas a width measure W2 of the defective portion 27 along a width measure WL2 of the lateral portion 26b have a great influence on the electricity-conductive function of the electricity-conducting path 26 in the example of FIG. 4B.

Thus, in this case, for the section corresponding to the longitudinal portion 26a of the electricity-conducting path 26, the maximum acceptable value with respect to the width measure W1 corresponding to the direction of crossing over the longitudinal portion 26a is set as a threshold value (i.e., acceptable level). For the section corresponding to the lateral portion 26b of the electricity-conducting path 26, the maximum acceptable value with respect to the width measure W2 corresponding to the direction of crossing over the lateral portion 26b is set as a threshold value (i.e., acceptable level). As described above, an inspection area including circuit component areas having the same function can be respectively divided into sections according to different acceptable levels corresponding to inspection conditions. Numbers of pixels on the monitor 19 may be used as the threshold values representing the acceptable levels.

Also, as inspection conditions, a square measure/number of a defective portion, a luminance level of an inspection area, a shape of a defective portion, a spatial frequency of a screen of an inspection area and the like can be set other than a measure (length) of a defective portion as described above. Layers may be respectively made as to those plural conditions and then sections having different inspection conditions can be made by superposing the layers.

The defect extracting portion 16b of arithmetic processing circuit 16 extracts a defective portion formed on the semiconductor chip 11a by comparing a surface image (21A) as a template with a surface image of the semiconductor chip 11a as a object to be inspected, as well-known in the prior art. The judging portion 16c of the arithmetic processing circuit 16 judges whether the defective portion extracted by the defect extracting portion 16b is acceptable or not.

As shown in FIG. 5A, when the defective portion 27 extracted by the defect extracting portion 16b spreads out over three sections 28a, 28b, 28c, each of which consists of for example an electricity-conducting path and which are divided by compartment lines Z1, Z2 composed of insulation material, the outer surface-inspecting apparatus 10 of the present invention selects, as a threshold value to be compared with the defect of the defective portion 27, the strictest threshold value of all the threshold values respectively set on the sections on which the defective portion is located and judges whether the defective portion 27 is acceptable or not by using the strictest threshold value.

In the example shown in FIG. 5B, inspection conditions 3-5 are respectively set on the sections 28a, 28b, 28c whose width measures of electricity-conducting paths increases in order of 28a, 28b, 28c. That is, the condition 3 is allotted to the section 28a having the narrowest width, the condition 5 is allotted to the section 28c having the widest width, and the condition 4 is allotted to the section 28b the middle-length in width. For example, if maximum numbers of pixels regarding acceptable defects are respectively allotted to the conditions 3-5, a small number (small numeral value) of pixels is allotted as a threshold value 'A' to the section 28a having the narrowest width in consideration of the degree of influence upon the section 28a relative to those of other sections. Also, intermediate number (intermediate numeral value) of pixels is allotted as a threshold value 'B' to the section 28b having a width wider than that of the section 28a, and a large number (large numeral value) of pixels which is larger than that of the section 28*b* is allotted as a threshold value 'C' to the section 28*c* having the widest width.

In this case, the judging portion 16*c* of the arithmetic processing circuit 16 detects sections 28*a*, 28*b*, 28*c* on which the defective portion 27 is located and compares each other the threshold values (the threshold value 'A', the threshold value 'B', the threshold value 'C') respectively set on the sections to select one threshold value representing the strictest condition, i.e. the threshold value 'A' representing the smallest number of pixels. The judging portion 16*c* compares the selected threshold value 'A' with the number of pixels corresponding to the defective portion 27. At this step, the numbers of pixels corresponding to parts of the defective portion 27 located on the compartment lines Z1, Z2 consisting of insulation material is not necessarily estimated.

In the case the number of pixels corresponding to the defective portion exceeds the threshold value 'A', the judging portion 16*c* drives the monitor 19 to display the judgment result where the semiconductor chip 11*a* as a to-be-inspected object is a defective product.

The process of the inspection method using the outer surface-inspecting apparatus 10 according to the present invention will be described below, referring to the flowchart shown in FIGS. 6A and 6B.

Figure 6A:
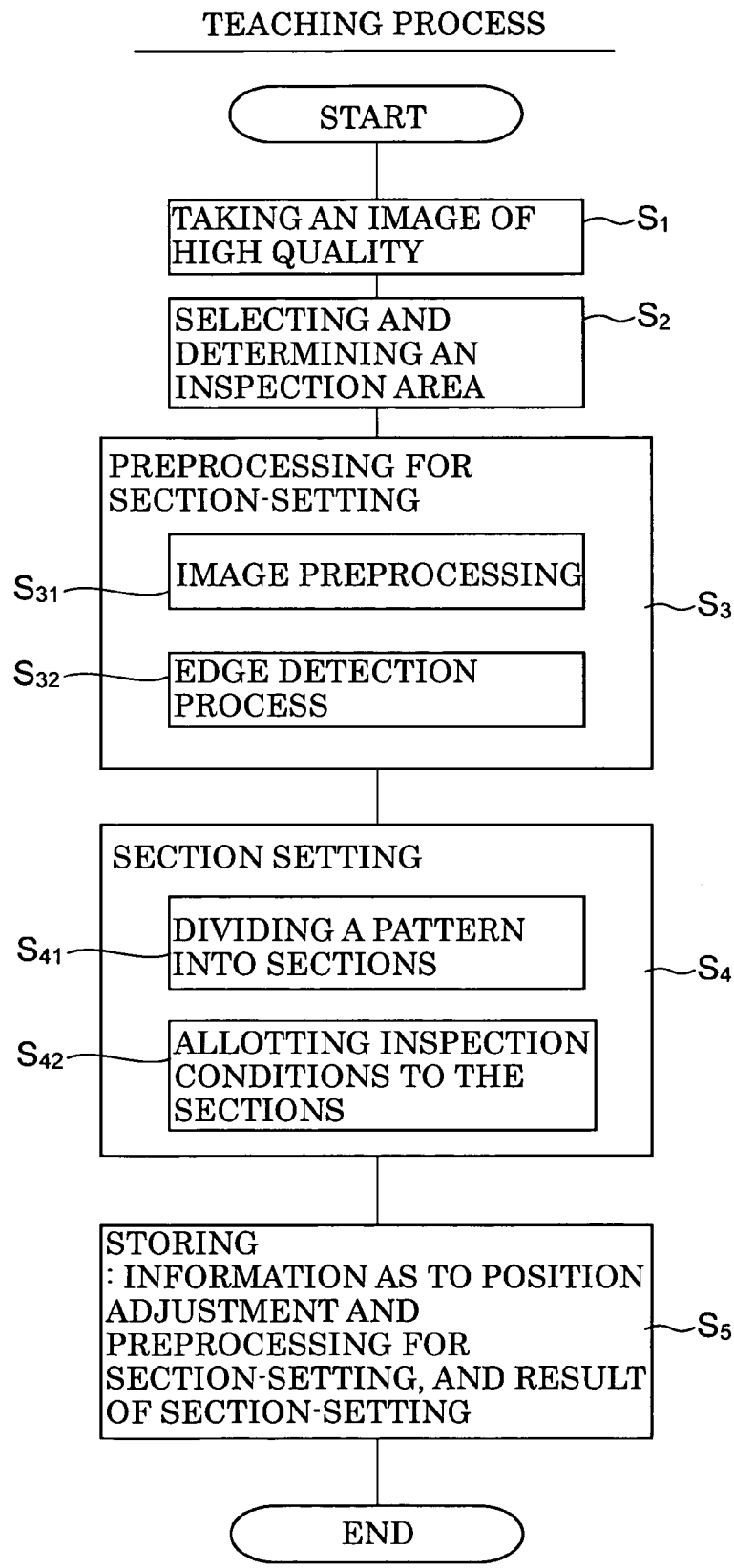
FIG. 6A is a flowchart showing a teaching process of the outer surface-inspecting method according to the present invention.
Figure 6B:
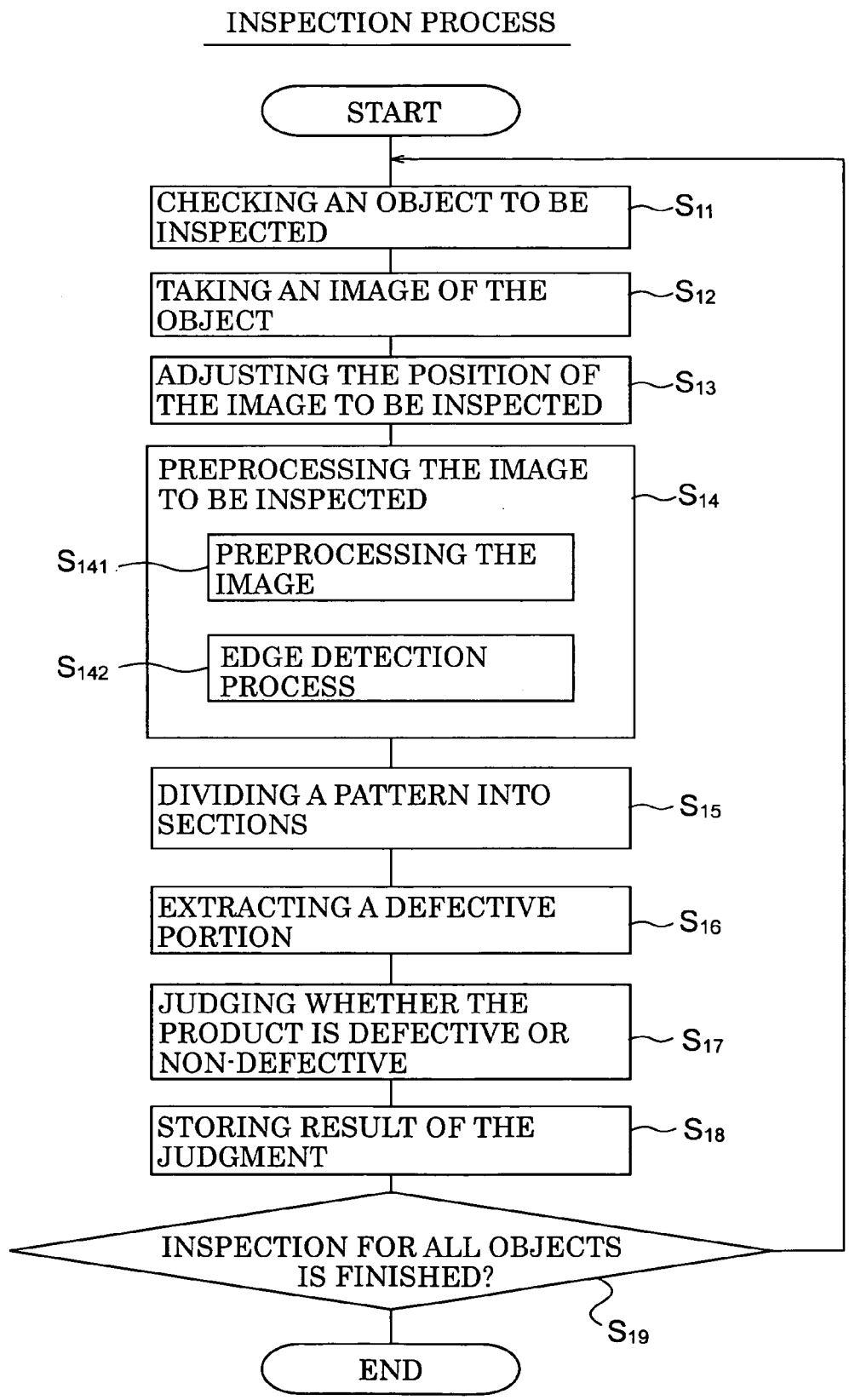
FIG. 6B is a flowchart showing an inspecting process of the outer surface-inspecting method according to the present invention.

FIG. 6A shows a teaching process for obtaining a template, and FIG. 6B shows a inspection process using the template obtained by the teaching process.

In the teaching process a surface image of the semiconductor chips 11*a* of the semiconductor wafer 11 disposed on the stage 12*a* is taken by the image-pickup portion 15 and is displayed on the monitor 19. An operator refers to the taken image displayed on the monitor 19 and selects a semiconductor chip 11*a* of high quality having fewer defects therein, and then a surface image of the selected semiconductor chip 11*a* is taken by the image-pickup portion 15 (Step S1).

A surface image corresponding to a desired inspection area is selected as a template from the taken surface image. By this step, a surface image of the inspection area having fewer defects therein corresponding to, e.g., the surface image 21A in FIG. 3A is obtained (Step S2).

Before setting sections on the surface image (21A), i.e., before setting sections on the template selected at Step S2, the surface image (21A) is preprocessed for section-setting by the arithmetic processing circuit 16 (Step S3). For this preprocessing for section-setting, e.g., a shading process for diminishing unevenness of lighting, an expansion-contraction process for reducing noise and the like are performed as an image preprocessing on the surface image (21A) by the arithmetic processing circuit 16 (Step S31), and then an edge detection process using e.g., differentiation is carried out by the arithmetic processing circuit 16 (Step S32). By the edge detection process a pattern of the inspection area is enabled to be detected by the arithmetic processing circuit 16. Thus the circuit pattern of the inspection area is determined.

Figure 3B:
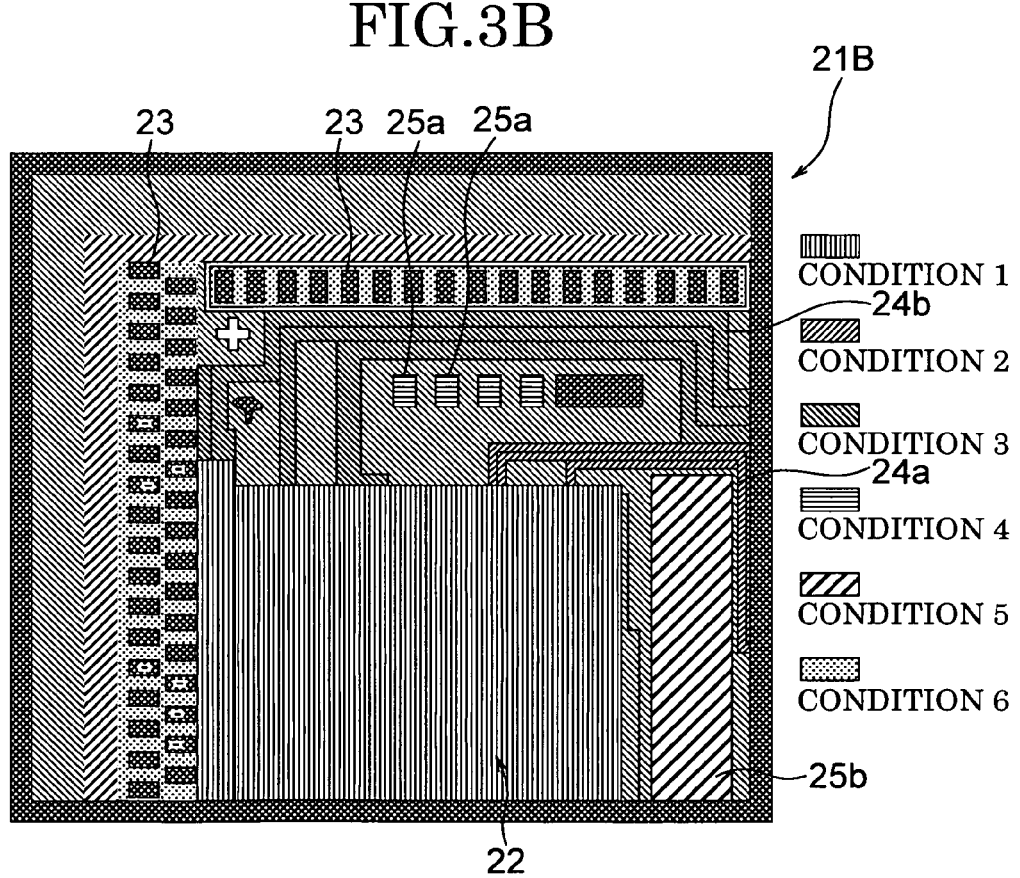
FIG. 3B is an explanatory view showing an example of set sections of a pattern image obtained by the image shown in FIG. 3A through an edge detection process.

After the completion of the preprocessing for section-setting at Step S3, a process for section-setting is performed on the surface image by the section-setting portion 16*a* of the arithmetic processing circuit 16 (Step S4). In this section-setting process, as shown in FIG. 3B, the circuit pattern of the inspection area detected by the arithmetic processing circuit 16 is divided into sections (22, 23, 24*a*, 24*b*, 25*a*, 25*b*) (Step S41), and threshold values respectively corresponding to inspection conditions (1-6) as described above are allotted to the corresponding divided sections (22, 23, 24*a*, 24*b*, 25*a*, 25*b*). Accordingly, the section-setting process is completed. On the completion of the section-setting process a template as a master pattern in the inspection process is obtained.

For defining sections at Step S41, the section-dividing scheme disclosed in Japan Patent Application Laid-Open No. 2004-85543 as mentioned above and/or the "layer scheme" disclosed in Japan Patent Application Laid-Open No. 2004-13295 can be used to simplify section-setting.

After the completion of the section-setting process, information as to the location of the selected inspection area determined at Step S2, information as to the result of the preprocessing for section-setting and information as to the result of the section-setting process (including the threshold values respectively allotted to the sections) at Step S3, etc. are stored in the memory 17 (Step S5) for the following inspection process, and then the teaching process ends.

Next, the inspection process using the template obtained by the teaching process will be described below referring to the flowchart shown in FIG. 6B.

In the inspection process, at first, the correspondence relationship between the semiconductor chip 11*a* as an object to be inspected and the template set in the outer surface-inspecting apparatus 10 is checked (Step S11). If there is no template corresponding to an object to be inspected, then a proper template can be obtained by the above-described teaching process.

After the correspondence relationship between the semiconductor chip 11*a* as an object to be inspected and the template set in the outer surface-inspecting apparatus 10 is confirmed at Step S11, a to-be-inspected image of the semiconductor chip 11*a* as an object to be inspected is taken by the image-pickup portion 15 (Step S12), and a position adjustment is performed for clipping a surface image corresponding to the template out of the to-be-inspected image (Step S13).

Information stored in the memory 17 at Step S5 in the teaching process is read out and is used for the image-pickup at Step S12 and the position adjustment at Step S13. Thus, the image of the semiconductor chip 11*a* of the object to be inspected is taken at Step S12 under the same condition of Step S1 in which the template is obtained (for example, the lighting condition of the lighting device 14, etc.).

After the to-be-inspected image corresponding to the template is clipped out of the inspection image by the position adjustment at Step S13, a preprocessing for a to-be-inspected image is carried out on the clipped surface image 21A (Step S14). The preprocessing for a to-be-inspected image is the same as the preprocessing for section-setting at Step S3 in the teaching process. Thereby, the pattern of the inspection area is detected.

The preprocessing for a to-be-inspected image (Step S14) includes an image preprocessing (Step S141) and an edge detection process (Step S142) which are respectively the same as the image preprocessing (Step S31) and the edge detection process (Step S32) in the preprocessing for section-setting (Step S3). In the image preprocessing at Step 141 and the edge detection process at Step S142, as similarly to S12, information as to the preprocessing for section setting at Steps S31, S32 stored in the memory 17 is read out. Then the preprocessing for a to-be-inspected image which is the same as the processes at Step S3 is executed on the surface image 21A under the same conditions of the image preprocessing (Step S31) and the edge detection process (Step S32) in the teaching process, according to the read-out information.

After the pattern of the inspection circuit is detected by the edge detection process at Step 142, the detected pattern is divided into sections according to the information as to contents of the section-setting read out from the memory 17 by the section-setting portion 16*a* of the arithmetic processing circuit 16, similarly to Step S41 in the teaching process. The inspection conditions are respectively allotted to the corresponding sections. By this step, the section-setting image 21B corresponding to the surface image 21A of the object to be inspected can be obtained as shown in FIG. 3B.

After the completion of Step S15, the surface image 21A of the object to be inspected and the template, both of which correspond to each other, are compared by the defect extracting portion 16b and a defective portion(s) on the surface image 21A is extracted through this comparison (Step S16).

The judging portion 16c judges whether a defect of each defective portion is acceptable or not based on comparison as to the acceptable level set on the defect of the each defective portion, e.g., comparison between the threshold value concerning a number (numeric value) of pixels and the number of pixels of the defect of the each defective portion (Step S17). Results of judgments whether the semiconductor chips 11a are defective or non-defective determined based on the result of the judgments as to defective portions are linked to the corresponding semiconductor chips 11a and are stored in the memory 17 (Step S18). The information (results) is displayed on the monitor 19.

At a following Step S19, whether any other semiconductor chip 11a as an object to be inspected exists or not is judged. In the case where another semiconductor chip 11a exists, the process returns to Step 11 and Steps 11 to 18 are carried out as described above. In the case where there is no semiconductor chip 11a as an object to be inspected, the inspection process is finished.

The judging process (Step S17) of the inspection process according to the present invention will be described in more detail below.

When a defective portion is extracted at Step S16 antecedent to the judging process of Step S17, it is judged whether the extracted defective portion is located on a single set section or spreads out over plural set sections. This judgment may be carried out by way of observing the monitor 19 by an operator, or the judging portion 16c may automatically carry out the judgment with use of the information stored in the memory 17 at Step S5.

As to a defective portion located on a single set section, the judging portion 16c calculates the centroid of the defective portion like the conventional centroid method and then compares the threshold value (e.g., a numeric value of pixels) of the set section on which the centroid is located with the corresponding value (e.g., the number of pixels) of the defective portion. In the case where the number of the defective portion exceeds the threshold value of the corresponding set section, the fact that the semiconductor chip 11a which is an object being inspected is a defective product is displayed on the monitor 19.

On the other hand, if it is judged that the defective portion spreads out over plural set sections, threshold values of all sections on which the defective portion is located are compared with each other and a threshold value corresponding to the strictest condition is selected. Whether the defective portion is acceptable or not is judged with the selected threshold value. If the defective portion is judged unacceptable, the judging portion 16c displays to the monitor 19 the judgment result indicating the semiconductor chip 11a as a to-be-inspected object is a defective product, as described above.

In the case the defective portion spreads out over plural set sections, the defective portion may be preliminarily judged by the conventional centroid method and by the above-described method where a threshold value having the strictest inspection condition of all sections on which the defective portion is located, and the final judgment can be made by using both preliminary judgment results. By so doing, more correct inspection can be carried out.

As described above, when a defective portion spreads out over more than one section, whether the defective portion is acceptable or not is judged with use of an acceptable level corresponding to the strictest inspecting condition of all the sections on which the defective portion is located. Thus, even if a part of the defective portion being located on the section corresponding to the strictest inspecting condition does not have therein the centroid of the defective portion, the defective portion is judged with use of the threshold value corresponding to the strictest inspecting condition. Thus, an overlooked error as to a defect of a part of a defective portion whose centroid is out of the part can be eliminated. Therefore, comparing to the prior surface inspecting method, defective products can be found without fail regardless of the position of the centroid of the defective portion.

Further, a more proper judgment according to a situation can be carried out in conjunction with the conventional centroid method.

What is claimed is:

1. An outer surface-inspecting method for judging whether a defect of a defective portion extracted from an inspection area in an image of an object to be inspected through comparison with a template is acceptable or not, comprising:
    dividing the inspection area into a plurality of sections respectively in which threshold values of different acceptable numbers of defective pixels representing different acceptable levels;
    judging whether at least one extracted defective portion is located over plural sections having different acceptable levels or within a single section;
    comparing the threshold values of the plural sections with pixel numbers of the image and selecting the threshold value of the lowest acceptable number of defective pixels set in the plural sections when the at least one extracted defective portion is located over the plural sections;
    calculating a centroid of the at least one extracted defective portion and selecting the acceptable level of the single section on which the centroid is located when the at least one extracted defective portion is located within a single section; and
    judging whether the defect of the defective portion is acceptable or not based on the selected threshold value of the lowest acceptable number of defective pixels set in the sections.

2. The outer surface-inspecting method according to claim 1, further comprising judging whether the defect of the defective portion located over the plurality of the sections is acceptable or not with use of the acceptable level of the section on which a centroid of the defective portion is located, wherein whether the defect of the defective portion is acceptable or not is judged through comparison of the result of the judgment made based on the selected acceptable level and the result of the judgment made with use of the acceptable level of the section on which the centroid is located.

3. The outer surface-inspecting method according to claim 1, wherein the sections are set based on superposition of layers respectively formed in conformity with different inspection conditions as to a defect.

4. An outer surface-inspecting apparatus comprising:
    an image-pickup portion configured to obtain an image of an object to be inspected;
    an arithmetic calculation processing circuit configured to carry out an edge detection process on the image obtained by the image-pickup portion; and a monitor configured to display the image obtained by the image-pickup portion and the image processed by the arithmetic calculation processing circuit, wherein the arithmetic calculation processing circuit includes:

a section-setting portion configured to divide an inspection area of a pattern image obtained through the edge detection process into a plurality of sections to which different threshold values of different acceptable numbers of defective pixels representing acceptable levels as to a defect are respectively allotted;

a defect-extracting portion configured to extract a defective portion of the object to be inspected by comparing a template to the image of the object to be inspected; and a judging portion configured to judge whether the extracted defective portion is located over plural sections or within a single section, to compare, when the extracted defective portion is located over the plural sections, all the threshold values respectively set on the sections on which the defective portion extracted by the defect-extracting portion is located with pixel numbers of the image, to select the threshold value of the lowest acceptable number of defective pixels set in the sections, and configured to output a result of the comparison to the monitor, and to calculate a centroid of the at least one extracted defective portion and select the acceptable level of the single section on which the centroid is located when the extracted defective portion is located in the single section, wherein the judging portion is configured to judge whether the defect of the defective portion is acceptable or not based on the selected threshold value of the lowest acceptable number of defective pixels set in the sections when the extracted defective portion is located over the plural sections.

* * * * *